United States Patent [19]

Steiger et al.

[11] Patent Number: 5,265,461
[45] Date of Patent: Nov. 30, 1993

[54] APPARATUSES AND METHODS FOR MEASURING ULTRASONIC VELOCITIES IN MATERIALS

[75] Inventors: Ronald P. Steiger, Houston; Peter K. Leung, Sugar Land, both of Tex.; Rudolf J. Stankovich, Park City, Utah

[73] Assignee: Exxon Production Research Company, Houston, Tex.

[21] Appl. No.: 671,367

[22] Filed: Mar. 19, 1991

[51] Int. Cl.[5] .................... G01N 29/18; G01N 29/22
[52] U.S. Cl. ........................... 73/38; 73/594; 73/597; 73/73; 73/794
[58] Field of Search .............. 73/594, 597, 571, 579, 73/38, 862.65, 856, 73, 794

[56] References Cited

U.S. PATENT DOCUMENTS

| | | | |
|---|---|---|---|
| 3,199,341 | 8/1965 | Heuer, Jr. et al. | 73/820 |
| 3,313,151 | 4/1967 | Kaye | 73/862.65 |
| 3,421,366 | 1/1969 | Ely | 73/819 |
| 3,423,994 | 1/1969 | Scott et al. | 73/819 |
| 3,423,995 | 1/1969 | Scott et al. | 73/819 |
| 3,457,777 | 7/1969 | Nielsen | 73/84 |
| 3,505,860 | 4/1970 | Bishop et al. | 73/819 |
| 3,537,541 | 11/1970 | Desai | 73/594 |
| 3,610,032 | 10/1971 | Di Crispino | 73/819 |
| 3,616,685 | 11/1971 | Strom | 73/819 |
| 3,635,078 | 1/1972 | Wissa | 73/89 |
| 3,728,895 | 4/1973 | Shaw | 73/94 |
| 3,820,385 | 6/1974 | Crodoba | 73/84 |
| 3,881,345 | 5/1975 | Souder | 73/94 |
| 3,975,950 | 8/1976 | Erdei | 73/94 |
| 4,380,930 | 4/1983 | Podhrasky et al. | 73/594 |
| 4,430,890 | 2/1984 | Hains | 73/147 |
| 4,487,056 | 12/1984 | Wiley | 73/38 |
| 4,502,338 | 3/1985 | Smith et al. | 73/819 |
| 4,506,542 | 3/1985 | Rose | 73/38 |
| 4,561,289 | 12/1985 | Jones | 73/38 |
| 4,562,726 | 1/1986 | Barnaby | 73/38 |
| 4,587,857 | 5/1986 | Bush | 73/863 |
| 4,599,891 | 7/1986 | Brauer et al. | 73/38 |
| 4,607,532 | 8/1986 | Arthur et al. | 73/819 |
| 4,627,270 | 12/1986 | Jones | 73/38 |

(List continued on next page.)

FOREIGN PATENT DOCUMENTS

0080534 5/1983 Japan .................... 73/862.65

OTHER PUBLICATIONS

"Lateral-deformation Gage for Rock-mechanics Testing" by Karl W. Schuler (Experimental Mechanics) pp. 477-480, vol. 18 No. 12 (Dec. 1978).

"Quantitative Determination of The Mechanical Properties of Shales," Steiger and Leung, SPE Conference, Oct. 2-5, 1988.

"Predictions of Wellbore Stability In Shale Formations At Great Depth," Steiger and Leung, SPE Symposium 1989.

"Acoustical Properties of Clay Bearing Rocks," C. A. Tosaya, 1982.

"Drilling Fluids," Exxon Production Research Company, 1989.

(List continued on next page.)

*Primary Examiner*—Hezron E. Williams
*Assistant Examiner*—Rose M. Finley
*Attorney, Agent, or Firm*—Guy McClung

[57] ABSTRACT

Methods and apparatuses for measuring ultrasonic velocities in materials are disclosed which, in one embodiment, include such methods and apparatuses for triaxial tests of low permeability rock samples, the apparatus including top and bottom end caps for mounting to a sample to be tested, each end cap having an ultrasonic transducer mounted therein for disposition in contact with the material to be tested for measuring the velocities of ultrasonic waves through the material. In another embodiment, at least one end cap having channels and a sensor for sensing changes in sample pore pressure is disclosed. In another aspect, a pressure generator or microaccumulator for changing the amount of a pore pressure fluid in the channels, thereby changing sample water content and making possible an efficient multistage test is disclosed. In another embodiment an end cap for such measurements is disclosed.

5 Claims, 11 Drawing Sheets

U.S. PATENT DOCUMENTS

| | | | |
|---|---|---|---|
| 4,631,677 | 12/1986 | Park et al. | 364/422 |
| 4,638,447 | 1/1987 | Odeh | 364/556 |
| 4,643,019 | 2/1987 | Jones | 73/38 |
| 4,648,261 | 3/1987 | Thompson et al. | 73/38 |
| 4,649,737 | 3/1987 | Jones | 73/38 |
| 4,669,299 | 6/1987 | Closmann | 73/38 |
| 4,679,421 | 7/1987 | Barree | 73/38 |
| 4,679,441 | 7/1987 | Johnson et al. | 73/798 |
| 4,710,948 | 12/1987 | Withjack | 378/208 |
| 4,715,212 | 12/1987 | Johanson | 73/38 |
| 4,753,107 | 6/1988 | Reed et al. | 73/38 |
| 4,762,003 | 8/1988 | Cioletti | 73/825 |
| 4,791,822 | 12/1988 | Penny | 73/865 |
| 4,799,382 | 1/1989 | Sprunt et al. | 73/153 |
| 4,807,465 | 2/1989 | Botzolakis et al. | 73/78 |
| 4,825,700 | 5/1989 | Vardoulakis et al. | 73/749 |
| 4,827,761 | 5/1989 | Vinegar et al. | 73/38 |
| 4,845,995 | 7/1989 | Kaste et al. | 73/794 |
| 4,848,145 | 7/1989 | Blaschke et al. | 73/153 |
| 4,856,341 | 8/1989 | Vinegar et al. | 73/798 |
| 4,864,846 | 9/1989 | Jones | 73/38 |
| 4,868,751 | 9/1989 | Dogru et al. | 364/422 |
| 4,884,438 | 12/1989 | Jones et al. | 73/153 |
| 4,885,941 | 12/1989 | Vardoulakis et al. | 73/794 |
| 4,955,237 | 9/1990 | Suzuki et al. | 73/784 |
| 4,957,001 | 9/1990 | Powell | 73/716 |
| 4,961,343 | 10/1990 | Boone | 73/152 |
| 5,018,396 | 5/1991 | Penny | 73/865.6 |
| 5,025,668 | 6/1991 | Sarda et al. | 73/795 |
| 5,025,669 | 6/1991 | Sarda et al. | 73/798 |

OTHER PUBLICATIONS

"The Mechanics of Soils," Atkinson et al. 1978, pp. 118–144, 184–209, 292–343.

"Soil Mechanics," Lambe et al., 1969, Chapter 20, pp. 295–303.

"Fundamentals of Potassium Drilling Fluids: A Field Manual to Reduce Drilling and Completion Problems Associated with Hydratable Clays," Steiger, et al., 1985.

APPARATUSES AND METHODS FOR MEASURING ULTRASONIC VELOCITIES IN MATERIALS

BACKGROUND OF THE INVENTION

1. Field of the Invention

This invention is related to the measurement of ultrasonic velocities in materials. In one aspect this invention is directed to triaxial test apparatuses and methods employing ultrasonic transducers to measure ultrasonic velocities of low permeability rocks during a triaxial test.

2. Description of Related Art

A conventional triaxial test apparatus for rock testing is shown in FIG. 1. With such an apparatus, a test is performed inside an enclosed housing or hydraulic cell. A confining fluid is pumped into the test cell to provide a confining pressure on a rock sample specimen. The sample is placed on a bottom end cap for support. Hydraulic pressure is applied around the sample during the test to generate an isostatic confining stress. Then an axial load is applied (e.g. by a load piston) to a top end cap to generate a deviatoric (shear) stress.

Ultrasonic transducers have been used within end caps near opposite sides of a rock sample during tests. Ultrasonic waves from such transducers must pass through the end cap material, a material (usually metal) which alters the ultrasonic waves and affects them differently from the manner in which they are propagated through the material to be tested. This results in errors in measurement of velocity.

Applicants are unaware of any prior art disclosing test apparatuses and methods for materials which employ ultrasonic transducers adjacent the material to be tested to measure ultrasonic velocity in the material during a test.

There has long been a need for test apparatuses and methods for accurately measuring ultrasonic velocities of materials in which ultrasonic waves are not attenuated when going through material other than the material to be tested. There has long been a need for triaxial test apparatuses and methods which effectively and accurately measure ultrasonic velocities while simultaneously measuring pore pressure of a sample.

SUMMARY OF THE PRESENT INVENTION

Our invention includes a new design of triaxial test apparatus which includes end caps and test procedures to measure ultrasonic velocities while simultaneously measuring pore pressure in a material, e.g. but not limited to rock, composites, soils, concrete, and granular masses. The end caps have an ultrasonic transducer partially disposed therein with an exposed portion adjacent a material to be tested which provides sending or receiving capacity for ultrasonic waves (both p-wave and s-wave).

In one embodiment of a triaxial test apparatus according to the present invention, a rock sample mounting apparatus is provided which has a bottom end cap and a top end cap, each with a flat planar face for mounting below (bottom end cap) or above (top end cap) the flat face of the sample. In each end cap at the flat face is an ultrasonic transducer which, during testing, is adjacent the rock sample. One transducer is a transmitter and one is a receiver (either can receive or send). A pore pressure channel may extend from a surface of an end cap (either top or bottom) to a pore pressure port or chamber in the end cap so that sample fluid expelled from the rock sample during testing (e.g. water or some other fluid) flows into the pore pressure channel. It is inhibited from flowing out of the channel and, even if some minute amount of fluid would escape from the face of the sample adjacent the end cap surface, one or more impermeable flexible jackets covering the side wall of the sample and extending slightly over the end cap to which it is secured prevents sample fluid from exiting from the end-cap-face-of-the-rock-sample interface and into the continuing fluid.

Sample fluid expelled into the pore pressure channel contacts a pore pressure fluid (preferably a fluid not miscible with the sample fluid) and compresses it somewhat. That compression is sensed by a pore pressure transducer in the pore pressure port and it is conveyed in analog form (a change in voltage) via wiring from the pore pressure transducer to a monitor system (e.g. a computer which can also record data).

Deformations in the sample due to the load on it are measured using strain indicators; preferably linear variable differential transformers, for indicating vertical axial deformation and cantilevered strain gauges for indicating radial deformation. In one embodiment, the pore pressure channel and pore pressure port are very small and relatively little sample fluid is expelled from the sample (e.g. a shale) so that the sample-fluid content of the sample changes very little during the test, providing conclusive usable data.

In one embodiment utilizing a high pressure fluid generator or microaccumulator in communication with the pore pressure port, fluid can be withdrawn from a sample during testing by withdrawing pore pressure fluid from the pore pressure port during testing. In one embodiment, the top end cap also has a pore pressure channel with a port and in which is mounted a pore pressure transducer, the transducer having the associated wiring connectible to an external monitor-recording system. Thus, the fluid content of the sample can be adjusted and controlled during a test, thereby varying and controlling a sample's effective stress during testing. The end caps are, preferably, made from high strength material, e.g. hardened steel or titanium.

The traveling velocities (v) of ultrasonic waves, both compression (p-wave) and shear (s-wave) waves, through a rock sample are measured by sending waves from one side of the sample and receiving wave information from the other side of the sample. The ultrasonic wave measurements are performed, preferably, during a triaxial test, a compression test, or at the end of each stage of a multi-stage test, e.g. as described in the co-pending U.S. application Ser. No. 07/576,692 entitled "Apparatuses And Methods For Adjusting A Material's Fluid Content And Effective Stresses" a copy of which is submitted herewith and incorporated herein along with the materials incorporated therein. The ultrasonic velocities increase with effective mean stress applied on the sample. Consistent correlation between these two parameters (velocity and stress) can be observed.

In one embodiment, smaller transducers may be used if space is a consideration or if the rigidity of the end cap surface around an opening for a transducer is a consideration. In another embodiment, a relatively large transducer may be used which occupies a major portion of the end cap surface. In this embodiment, a pore pressure channel may extend through the transducer.

It is, therefore, an object of the present invention to provide new, useful, unique, efficient and nonobvious apparatuses and methods for measuring ultrasonic velocities in materials.

A further object of the present invention is the provision of new, useful, unique, efficient and nonobvious test apparatuses and methods for determining ultrasonic velocities in materials using members mountable in contact with the materials, the members having an ultrasonic transducer therein which is in contact with the material during the test.

The present invention recognizes and addresses the previously-mentioned long-felt needs and provides a satisfactory meeting of those needs in its various possible embodiments. To one of skill in this art who has the benefits of this invention's teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insure adequacy and aid understanding, this is not intended to prejudice that purpose of a patent which is to claim an invention no matter how others may later disguise it by variations in form or additions of further improvements.

DESCRIPTION OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings form a part of this specification. It is to be noted, however, that the appended drawings illustrate preferred embodiments of the invention and are therefore not to be considered limiting of its scope, for the invention may admit to other equally effective equivalent embodiments.

DESCRIPTION OF EMBODIMENTS PREFERRED AT THE TIME OF FILING FOR THIS PATENT

Figure 1:
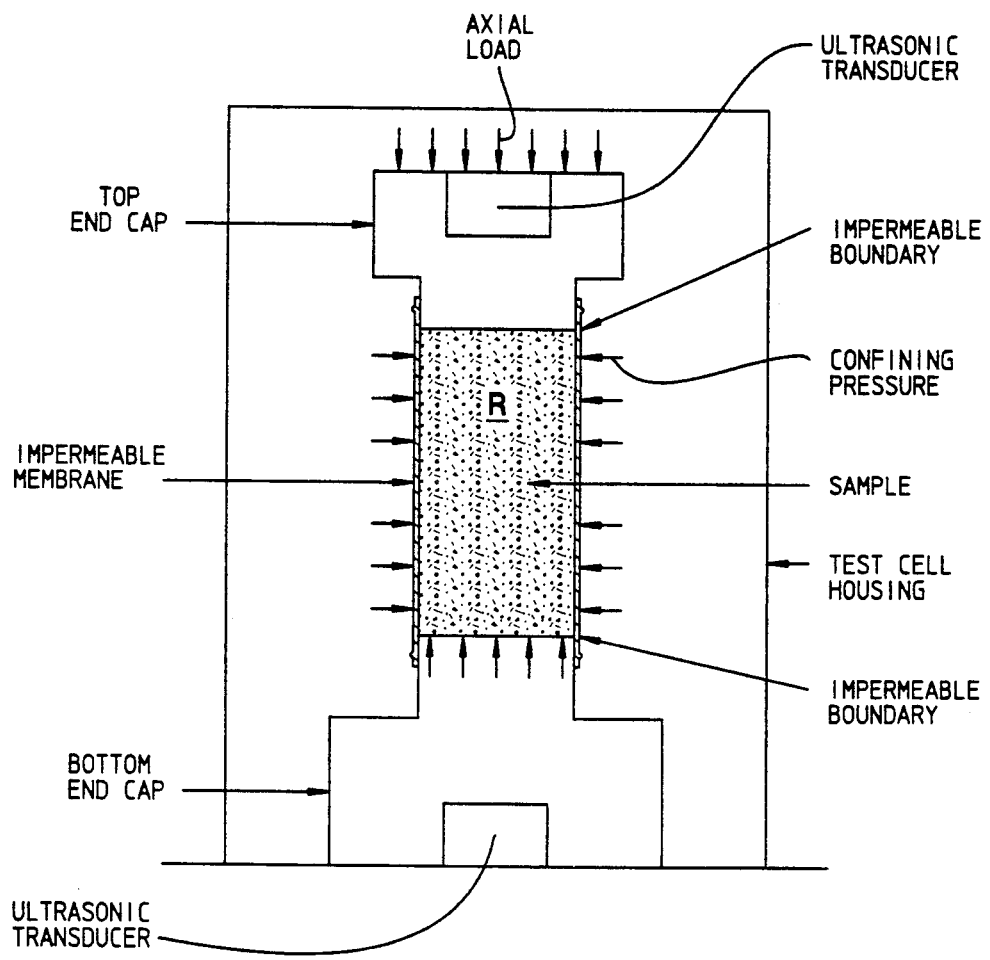
FIG. 1 is a schematic view of a prior art triaxial test apparatus.

Referring now to FIG. 1 a typical prior art triaxial test set-up is shown schematically. Mounting apparatus for a rock sample R include a top end cap and a bottom end cap. An impermeable membrane (e.g. a plastic or rubber jacket or jackets) is placed over the sample R. The jacket extends onto each end cap to which it is secured, e.g. by a wire rope, creating impermeable boundaries at each end of the sample R. Appropriate strain indicators are applied to the sample to indicate the extent of deformation of the sample during testing. The bottom end cap rests on a load cell (not shown) which indicates the amount of axial load applied to the sample R by a load piston (not shown). A confining fluid pumped into a sealed housing or test cell into which the mounted sample R is placed provides a desired confining pressure on the sample. This pressure is measured by a transducer (not shown) in the housing. Each end cap has an ultrasonic transducer therein, one of which transmits ultrasonic waves and one of which receives them. These waves pass through the metal of the end cap, through the sample R, and then through the metal of the opposite end cap.

Figure 2:
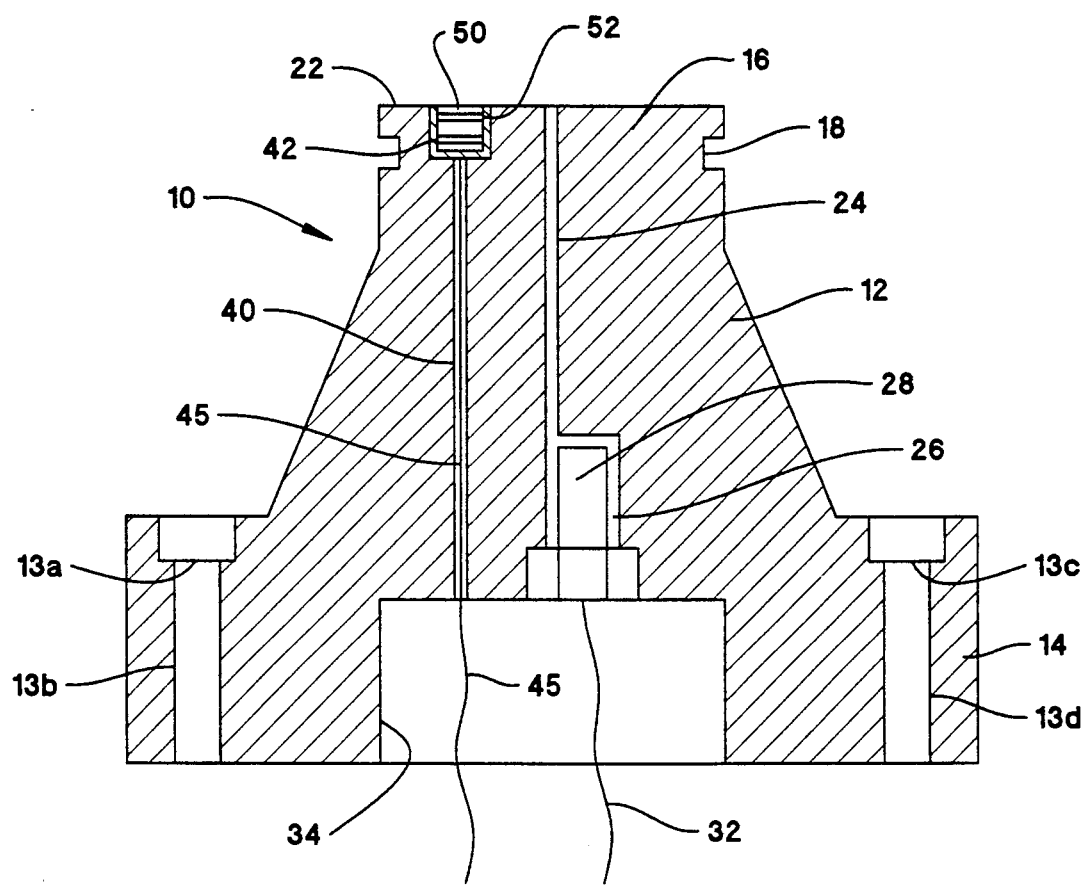
FIG. 2 is a side cross-sectional view of a triaxial test end cap according to the present invention.

An end cap 10 according to the present invention is shown in FIG. 2 in cross-section. The end cap 10 has a top portion 12 and a bottom portion 14 which are bolted together by bolts (not shown) extending through holes 13a, 13b, 13c, and 13d. An apex 16 of the top portion 12 has a groove 18 for receiving a portion of an impermeable flexible jacket or jackets (not shown) for enclosing the side of a rock sample.

A face 22 of the apex 16 is substantially flat for facing up against a flat surface of a rock sample; and it is preferred that the flatness of the face 22 vary only about 0.001 inch per inch of dimensional extent.

From the face 22 extends a pore pressure channel 24 in the end cap 10 which communicates with a pore pressure port 26 in the end cap 10. A pore pressure transducer 28 in the pore pressure port 26 senses changes in the pressure of a pore pressure fluid that fills the pore pressure port and the pore pressure channel. Sensed changes are conveyed via wiring 32 to a recorder or monitor (e.g. a digital data acquisition system or computer, now shown). The wiring 32 exits from the bottom portion 14 of the end cap 10 via a hole 34.

Sample fluid expelled from a rock sample mounted above the end cap 10 will move into the pore pressure channel 24 compressing a pore pressure fluid in the pore pressure channel 24 and in the pore pressure port 26. Preferably this pore pressure fluid is not miscible with the sample fluid; does not react with the sample or the sample fluid; is inert; and does not wet the sample. For example, if the sample fluid is water or oil, mercury is a preferred pore pressure fluid.

An ultrasonic transducer 50 is disposed in a recess 52 in the top portion 12 of the end cap 10. The ultrasonic transducer 50 is disposed at the face 22 of the apex 16 so that it is exposed and, during testing, is adjacent a portion of the surface of the sample being tested. A cup 42 surrounds the transducer 50 to inhibit electrical leakage from the transducer to the metal of the end cap and to prevent fluid from the sample from flowing into the channel 40. The cup 42 is preferably made from ceramic material because of its strength and rigidity and the fact that it is a nonconductor. To seal and secure the cup in place in the recess 52 a material such as epoxy may be used. Wiring 45 extends from the end cap through a channel 40 and into the hole 34 for interfacing with a monitoring/recording system (e.g. a computer).

Figure 3:
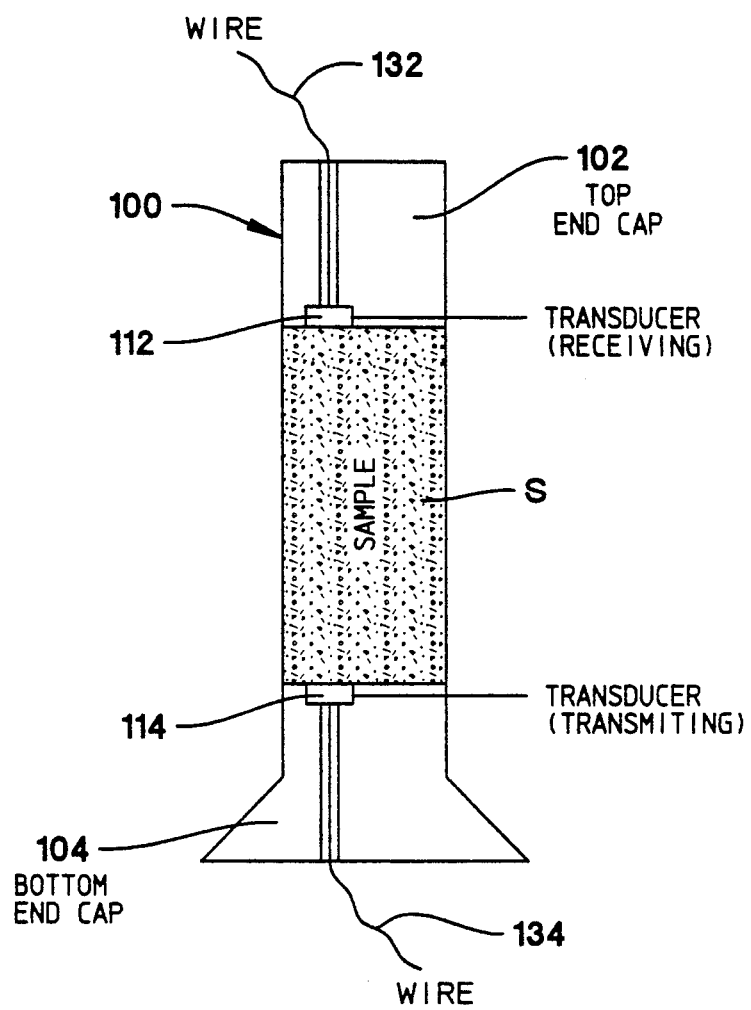
FIG. 3 is a side schematic view of a triaxial test apparatus according to the present invention.

FIG. 3 illustrates schematically, a test apparatus 100 according to the present invention which has a top end cap 102 and a bottom end cap 104 mounted to a rock sample specimen S to be tested in a triaxial test apparatus (e.g. like in FIG. 1).

Each end cap 102, 104 has an ultrasonic transducer 112, 114 respectively, disposed therein. These transducers and their related apparatus are like the transducer 50 of FIG. 2 and are located in their respective end caps as is the transducer 50 in the end cap 10. Wiring 132, 134 extends from the transducers for interfacing with a monitoring/recording system (e.g. a computer).

Figure 4:
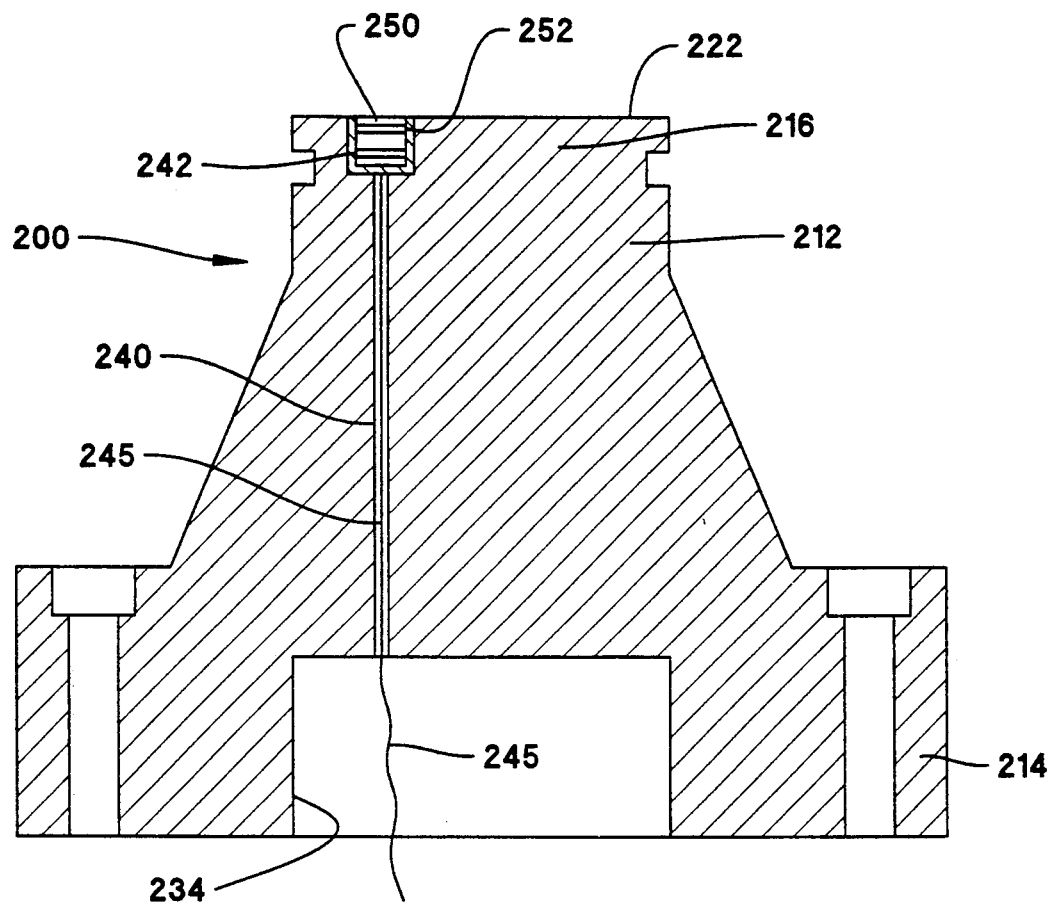
FIG. 4 is a side cross-sectional view of a triaxial test end cap according to the present invention.

FIG. 4 illustrates an end cap 200 according to the present invention which is like the end cap 10 (FIG. 2) but which has no pore pressure channel nor pore pressure transducer. The end cap 200 has a top portion 212 and a bottom portion 214 which can be bolted together. An ultrasonic transducer 250 is disposed in a recess 252 in the top portion 212 of the end cap 200. The transducer 250 is disposed at a face 222 of an apex 216 of the end cap so that the transducer is exposed and, during testing, is in contact with a sample being tested. In this matter, ultrasonic waves from the transducer do not traverse any metal in the end cap (or anything else for that matter unless there is something in a space between the transducer and the sample). Wiring 245 extends from the transducer 250 through a channel 240 in the end cap which communicates with a hole 234 into which the wiring extends and from which it exists for interfacing with a computer. A seal 242 acts as does the seal 42 (FIG. 1). When a dry sample is being tested, i.e., a sample with no fluid in it, no seal is needed. It should be noted that it is within the scope of the present invention to locate the transducer 250 anywhere on the face 222. One or both end caps are suitable for mounting to a load cell mounted within the housing, the load cell(s) for indicating the level of the load on the sample.

Figure 5:
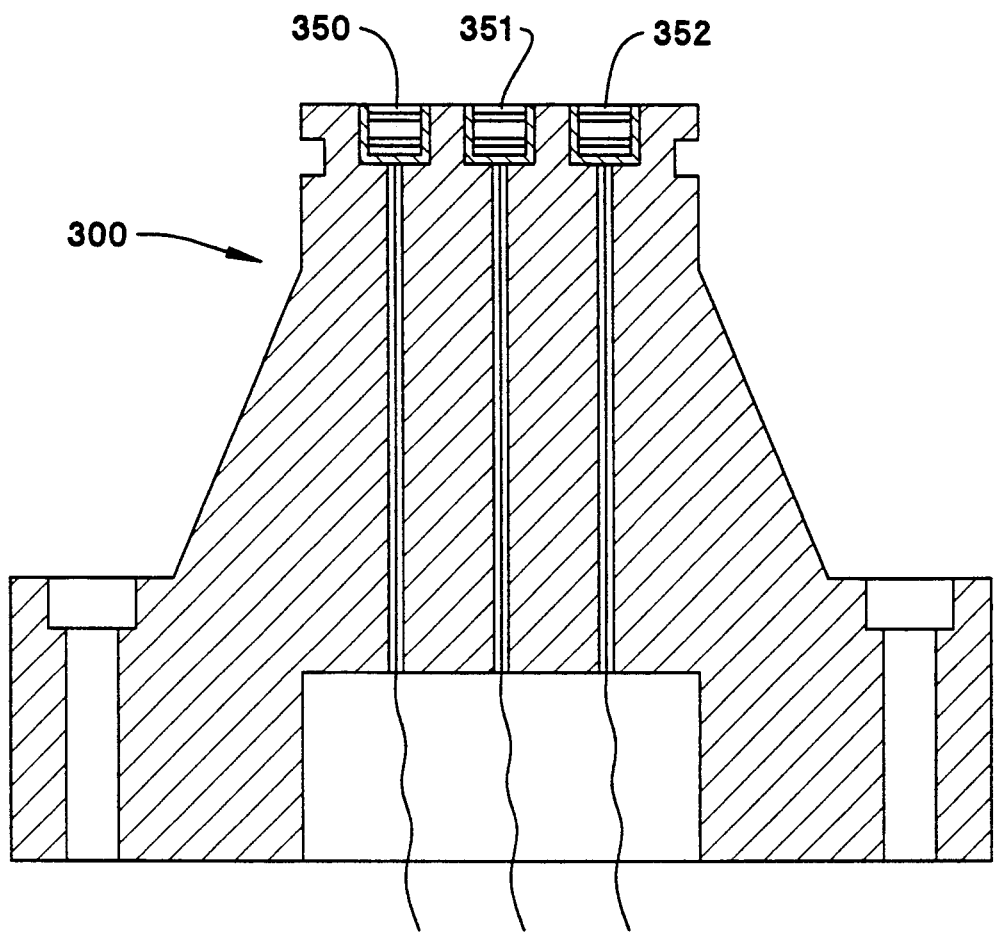
FIG. 5 is a side cross-sectional view of a triaxial test end cap according to the present invention.

FIG. 5 illustrates an end cap 300 which is similar to the end cap 200 (FIG. 4) but which has a plurality of ultrasonic transducers 350, 351, and 352. Such an end cap may be used with another end cap having three ultrasonic transducers or it may be used with an end cap having one transducer or a plurality (two or more) transducers.

Figure 6:
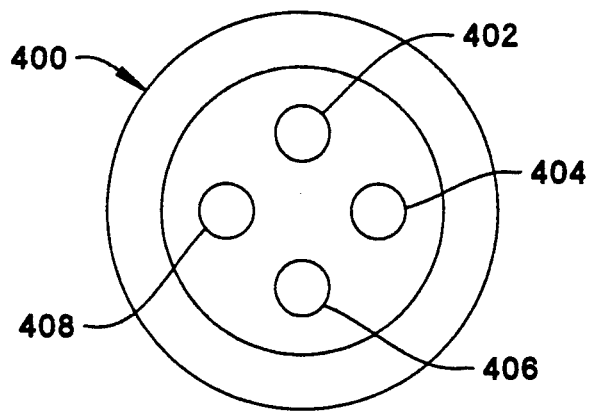
FIG. 6 is a top view of an end cap according to the present invention.

FIG. 6 shows an end cap 400 (similar to those previously described) according to the present invention with an array of ultrasonic transducers 402, 404, 406, and 408. Such an end cap is useful for testing sample homogeneity and for investigating failure mechanisms.

In one method according to the present invention a well preserved and undisturbed rock sample cored from a wellbore is mounted with end caps according to this invention. Then, a constant isostatic confining pressure, p, is applied on the rock sample in a triaxial cell. The sample's pore pressure is allowed to equilibrate, e.g. reach a constant value as the sample is consolidated under the cell's confining pressure. Pore pressure, u, is measured by a pore pressure sensor (e.g. pore pressure transducer 28, FIG. 2) in the pore pressure port and the effective (confining) stress, p', is defined as (p-u). The test can be performed in multi-stages. In each stage of a multi-stage test, a small amount of water is withdrawn from the sample by adjusting a high pressure generator or by adjusting a microaccumulator. This decreases the sample's water content by steps, thereby increasing its effective stress by steps, since lowering the sample's water content lowers its pore pressure. When one stage is completed and the water content has been reduced, time is again allowed for the sample's pore pressure to equilibrate. Once a substantially constant sample pore pressure is achieved, the next step of the loading is commenced. By calculating the sample water content and effective stress for each stage of the test, their relationship can be accurately defined in one multi-stage test.

The traveling velocity (v) of ultrasonic waves, both compression (p-wave) and shear (s-wave) waves, through the rock sample is measured by sending waves from one side of the sample and receiving wave information from the other side of the sample. The ultrasonic test is performed at the end of each stage of the compression test described above. The ultrasonic velocities increase with effective stress applied on the sample. Consistent correlation between these two parameters can be observed.

The present invention includes within its scope apparatuses (and methods using them) in which no high pressure generator or microaccumulator is used, but then the sample's fluid content cannot be adjusted or changed during the test, e.g., multi-stage step-wise tests on one sample are not done.

In one embodiment of this invention of a test method for triaxially testing rock sample, the sample is prepared and mounted by mounting a pore pressure transducer in a pore pressure chamber in a bottom end cap of a triaxial test apparatus, the pore pressure chamber in fluid communication with a pore pressure channel extending to a surface of the end cap for disposition contactingly adjacent the rock sample to be tested. The pore pressure channel is suitable for receiving sample fluid expelled from the sample during testing. Substantially all the air is evacuated from the pore pressure channel and from the pore pressure chamber and then they are filled with an inert fluid immiscible with the sample fluid. In a sealed chamber, a screen member is applied around the sample to facilitate the flow of sample fluid into the pore pressure channel and a flexible impermeable jacket is applied to the sample, other than to its ends. The bottom end cap is applied to the bottom end of the sample and a top end cap to the top end of the sample, each end cap having an ultrasonic transducer mounted in a recess therein with a portion of the transducer exposed and contacting the rock sample. Each ultrasonic transducer has transducer wiring leading therefrom connected to an exterior system for monitoring and recording signals from the sample. The test method includes: placing the sample in a confinement vessel of a triaxial test apparatus and sealing the vessel shut; isostatically loading the sample by introducing a confining fluid under pressure into the confinement vessel to provide a constant confining pressure on the sample; interconnecting the pore pressure transducer and the ultrasonic transducers with the exterior system; allowing the sample's pore pressure to equilibrate and reach a substantially constant level as the sample consolidates under the pressure of the confining fluid; applying a load piston to the top end cap to apply a known load on the sample, the piston sealingly extending through the confinement vessel to contact the sample; measuring and recording pore pressure of the sample continuously during the test; and measuring and recording ultrasonic velocity of ultrasonic waves transmitted from one ultrasonic transducer to the other through the sample continuously during the test.

This invention is directed to end caps with transducers which are not within the body of the end cap. Preferably, the transducers contact directly the material to be tested, but it is within the scope of this invention for the transducer to contact an intermediate material between the transducer and the material to be tested and the word "contact" or "contacting" in the appended claims may be so construed.

Figure 7:
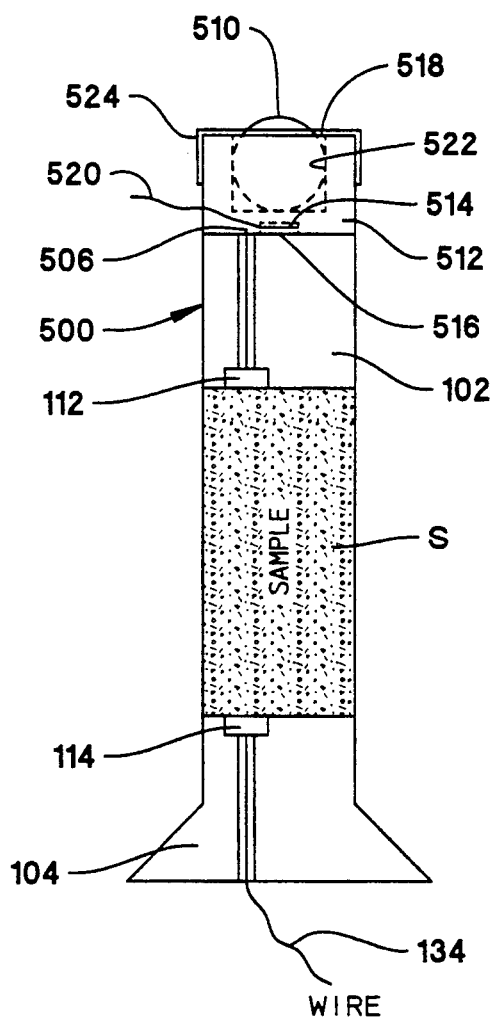
FIG. 7 is a side cross-sectional view of a triaxial test apparatus according to the present invention, including a top load cell.

A triaxial test apparatus 500 as shown in FIG. 7 is like the apparatus 100 (FIG. 3) and like numerals indicate like parts. The apparatus 500 has a top load cell 506 mounted on a top end cap 102. The cell 506 has a self-centering steel ball 510 disposed partially within recess 522 in a cylindrical steel frame 512. The ball 510 puts little or no torque on a sample to be tested and provides a relatively high stress at a center point of the frame 512, permitting sensitive accurate load measurement. A diaphragm strain gauge 514 is attached in a slot 516 in the bottom of the steel frame 512 at a point beneath the point at which the ball 510 contacts the frame 512. A load piston (not shown) contacts the ball 510 to impart a load through the top end cap 102 to a sample S. A plastic cap 516 fits snugly over the frame 512 and has a hole 518 in its top through which the ball 510 protrudes. The cap prevents the ball from coming out of the frame 512. A typical conventional diaphragm gauge (e.g. those provided by Micromeasurements Co.) may be used. Such gauges are accurate to about 2 to 10 psi in a load range of about 6000 to 8000 psi. The gauge's range can be increased to about 15,000 by changing the thickness of the cubical frame around the slot to (e.g. from 0.1 inch to 0.15 inch) and/or by using a diaphragm gauge with a higher range capability. Wiring 520 extends from the strain gauge, through a test cell housing (not shown), to interface with a monitoring and/or recording and/or controlling system (not shown).

Figure 8:
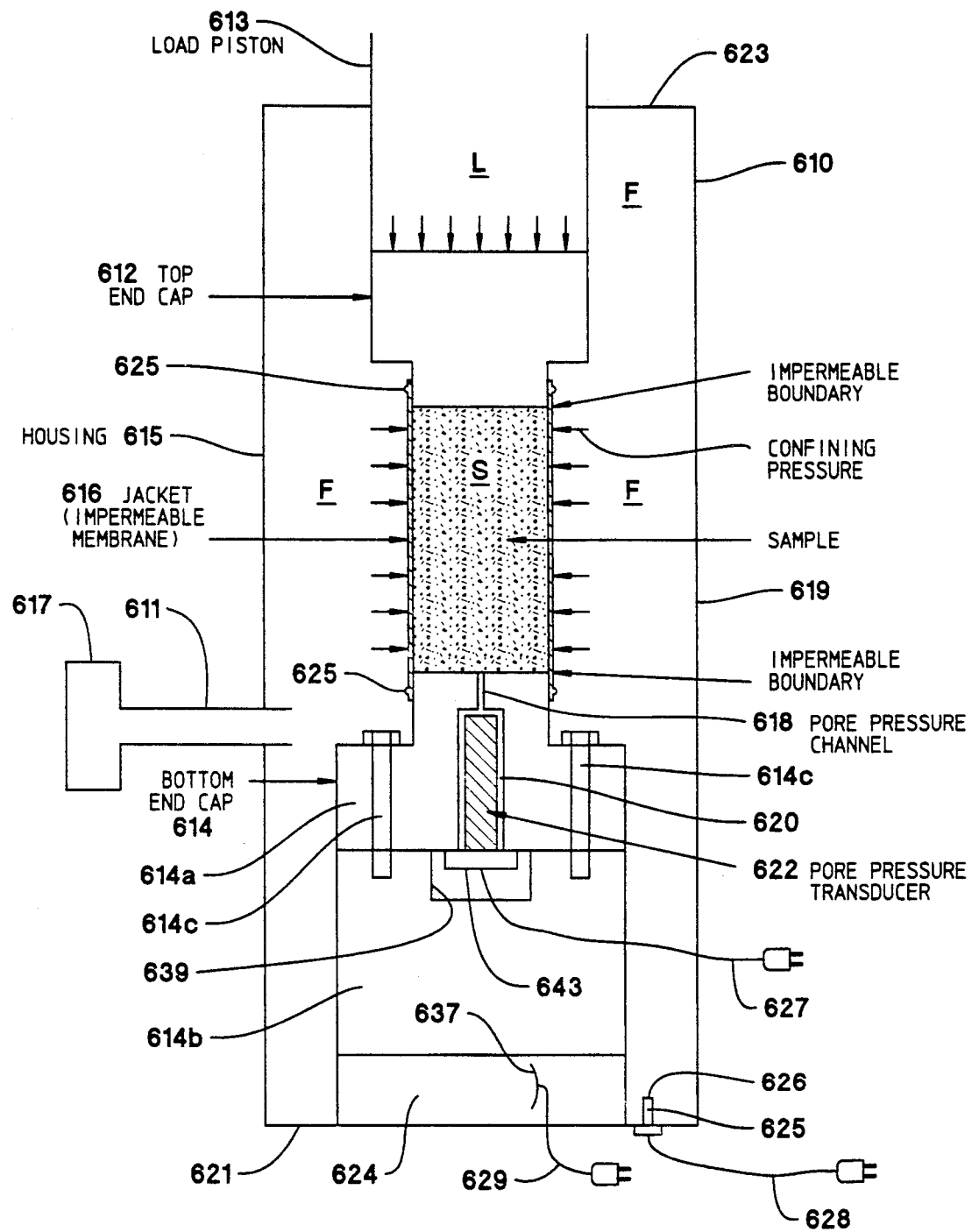
FIG. 8 is a schematic cross sectional view of a triaxial test apparatus according to the present invention.

As shown schematically in FIG. 8, a triaxial test apparatus 610 according to the present invention has a housing 615 preferably made from titanium or high strength steel with a side wall 619, (preferably generally cylindrical) a bottom plate 621, and a top plate 623. The apparatus 610 has a top end cap 612 and a bottom end cap 614. A sample S, placed between the caps, is sheathed with an impermeable jacket 616. A load piston 613 contacts the top end cap 612 and a portion of the piston extends sealingly through the top plate 623 of the housing 615. The load piston applies a load L to the sample S through the top end cap 612. A confining fluid pumping system 617 pumps an hydraulic fluid F into the housing 615 through a fluid line 611. As noted, additional jackets may be used. The end caps are made from high strength materials (e.g. titanium or hardened steel) and the boundaries between the end caps and the jacketed sample are impermeable. The jacket extend slightly beyond the sample on the end caps and wire ropes 625 secure the ends of the jacket about the end caps.

In a pore pressure port 642 of a pore pressure channel 640 is disposed a pore pressure transducer with wiring 646 which partially extends in a recess 644 of the top end cap 612. The end caps have flat, polished smooth surfaces for contacting the sample with diameters closely matched to that of the sample; i.e. it is preferred that they be within 0.005 inches of each other. Also, it is preferred that samples' ends' flatness be within about 0.001 inch per inch of diameter. This minimizes void space between end cap and sample; provides uniform loading of the sample; and minimizes unwanted end effects. The end caps may be as shown in FIGS. 2, 4, or 5 or as described above.

The bottom end cap 614 has a pore pressure channel 618 which communicates with a fluid port or chamber 620. A pore pressure transducer 622 is disposed in the fluid chamber 620. A non wetting inert fluid immiscible in water or pore fluid (e.g. mercury) is placed in the pore pressure channel 618 and in the fluid chamber 620. Preferably, the pore pressure channel 618 and the fluid chamber 620 are vacuum evacuated prior to the introduction of mercury so that no air is trapped therein which could adversely affect test results. The pore pressure transducer 622 is an accurate miniature strain gauge type pressure transducer interfaced via wiring 627 with a digital data acquisition system monitor/control (e.g. computer).

The hydraulic fluid F surrounding the sample S provides a desired confining pressure for the sample S. A confining pressure transducer 625 mounted in a hole 626 in the plate 621 has wiring 628 leading to the computer. The load cell 624 has wiring 629 extending therefrom for interfacing with the computer.

A high pressure generator or microaccumulator 8 is in fluid communication with the pore pressure chamber 20 via a stiff conduit 7, a channel 3, and a stiff conduit 4. A valve 5 controls flow in the conduit 7.

Figure 9:
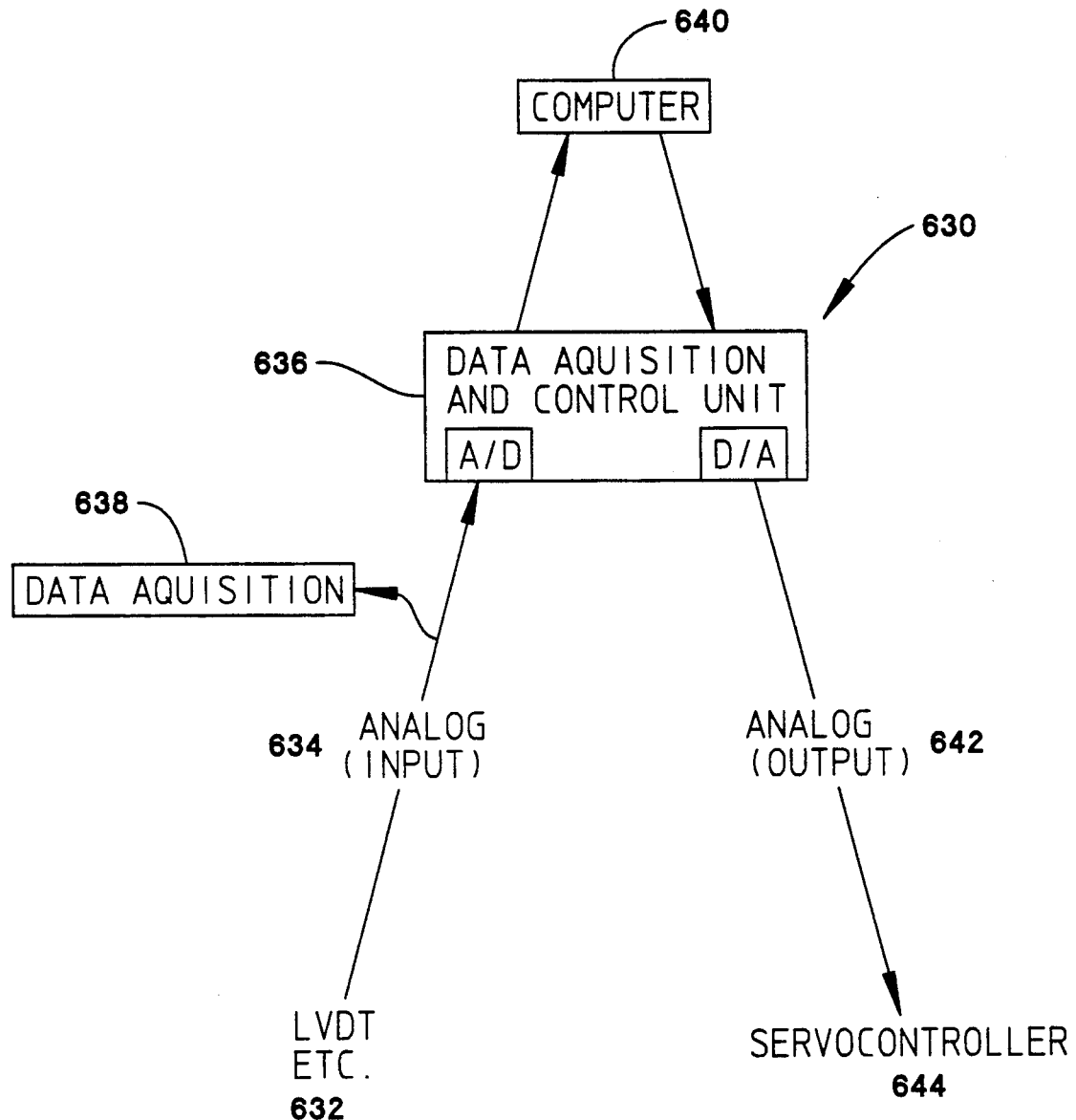
FIG. 9 presents in schematic form a data acquisition system.

Referring now to FIG. 9, a data acquisition and control system 630 is shown which is utilized with an apparatus such as the triaxial test apparatus 610 of FIG. 8 to control the rate of axial loading of a test specimen. An LVDT 632 or other measuring device such as a pore pressure transducer; confining pressure transducer; or radial strain transducer, provides analog signal input 634 to a data acquisition and control unit 636; e.g. a signal representative of axial strain within a certain time period. Input is also provided to data acquisition 638 for recording axial strain versus axial load. The data from unit 636, in digital form is provided to a computer 641 which compares the axial strain rate or strain within a certain time period to a chosen strain rate and sends a signal in digital form to the unit 636 which, in turn, provides an analog output signal 643 to operate servocontroller (or controllers) 645 which control valves to affect axial load.

Figure 10:
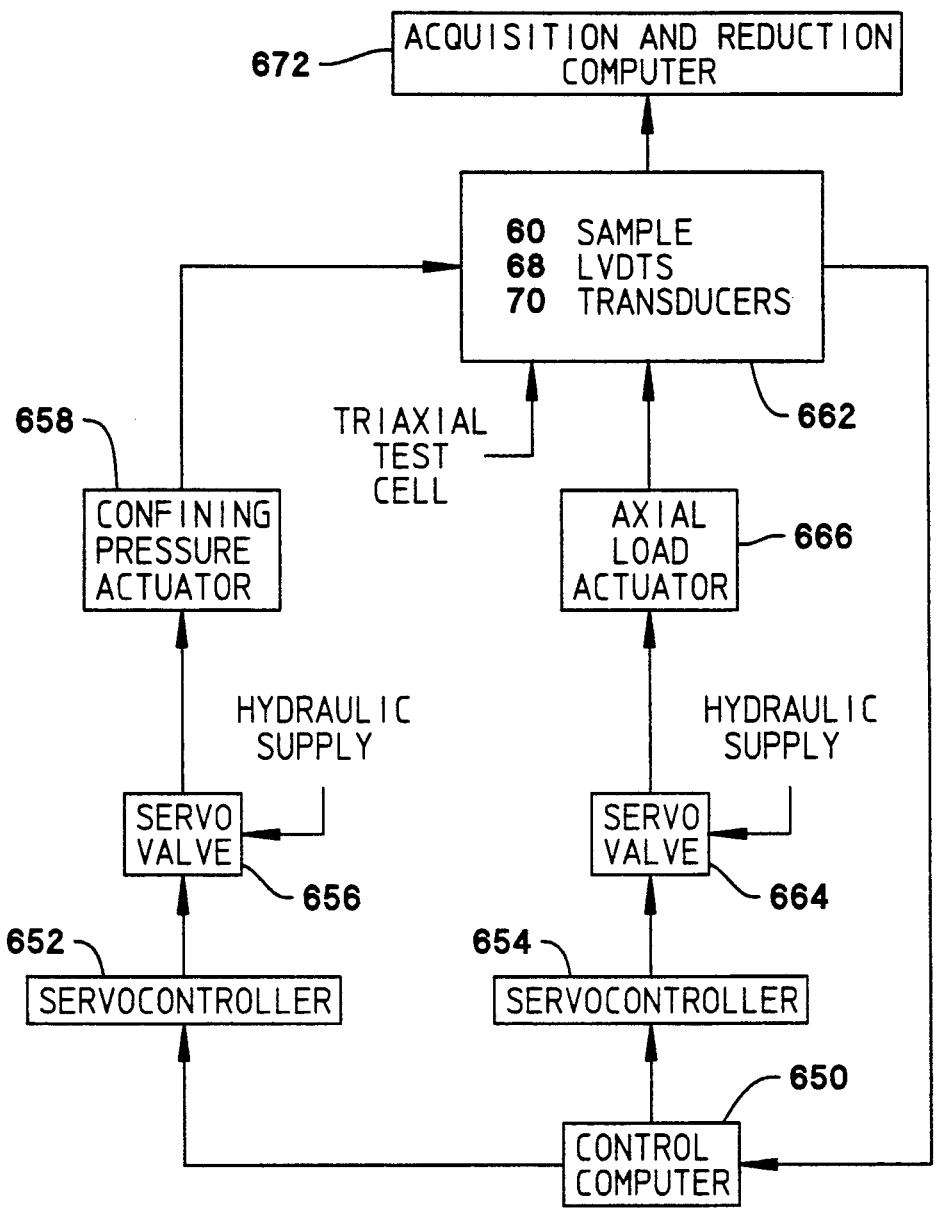
FIG. 10 presents schematically a computer control system.

As illustrated in FIG. 10, a control computer 650 (like the computer 640 of FIG. 9; e.g. an IBM AT PC computer) provides an analog output signal to servocontrollers 652 and 654. The servocontroller 652 controls a servovalve 656 which affects the supply of hydraulic fluid to a confining pressure actuator 658. The actuator 658 provides the pressurized hydraulic fluid about a test sample 660 in a triaxial test cell 662 like the apparatus 610 of FIG. 8.

The servocontroller 654 controls a servovalve 664 which affects the supply of hydraulic fluid to an axial load actuator 666. The actuator 666 provides pressurized fluid to a piston (not shown) which imparts an axial load to an end cap, such as the end cap 612 of the apparatus 610. The sample 660 may have various LVDT's 668 associated therewith, as well as transducers 670, which sense changes in the sample 660 and provide data to an acquisition and reduction computer 672 (like computer 640 in FIG. 9). A servocontroller 680 controls a servovalve 682 which affects the supply of hydraulic fluid to an accumulator activator 684. An accumulator LVDT 686 senses changes in the sample pore volume and provides data to the acquisition and reduction computer 672.

Figure 11:
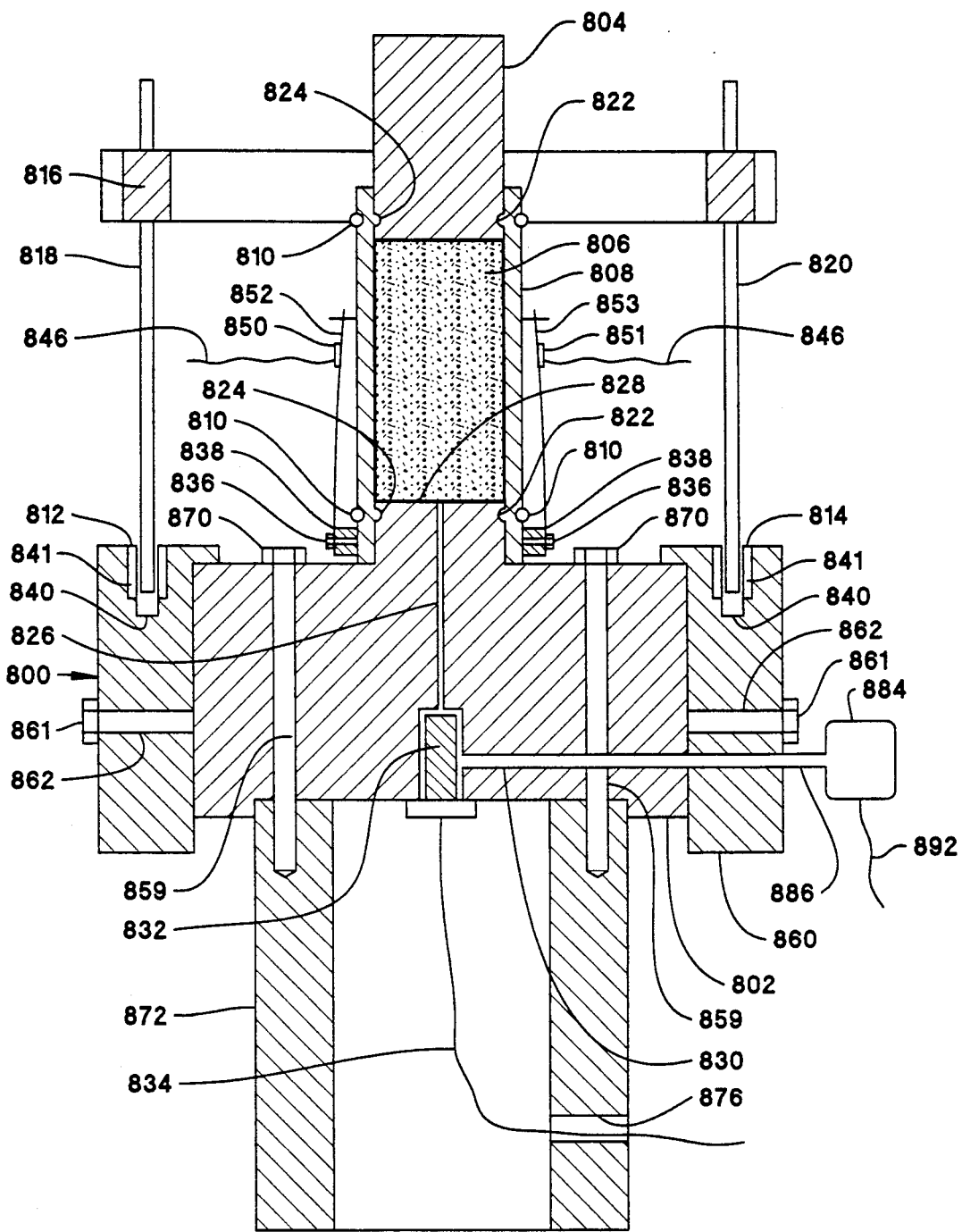
FIG. 11 is a cross sectional view of a test cell according to the present invention.

As shown in FIG. 11, a triaxial test cell apparatus 800 according to the present invention has a bottom end cap 802 and a top end cap 804. The end caps may be as shown in FIG. 2, 4, or 5 or as described above. A core sample 806 is mounted on the bottom end cap 802 and beneath the top end cap 804. A flexible impermeable jacket 808 sheaths the sample 806 and extends slightly beyond it onto each end cap. Lips 822 of the jacket 808 (or jackets if used) are received within corresponding grooves 824 in the end caps.

LVDT's 812 and 814 are disposed between the end caps and movably extend through holes 840 in a bottom collar 860 secured to the bottom end cap by set screws 861 through holes 862. LVDT rods 818 and 820 are secured to an LVDT holder 816 that is secured to the top end cap 804. The LVDT's 812, 814 indicate vertical movement of the end cap 804 due to axial movement (deformation) of the sample 806. The rods 818, 820 of the LVDT's are moveable in coils 841 in the bottom collar 860.

A pore pressure channel 826 extends from a top 828 of the bottom end cap 802 into a pore pressure chamber or port in which is disposed a pore pressure transducer 832. Wiring 834 extends from the pore pressure transducer into the base 872 and out through aperture 876 for interfacing the transducer with other equipment, e.g. a computer or other control/monitor/recording system. Screws 836 secure a radial strain gauge ring 838 about the bottom end cap 802. Radial strain gauges indicate radial deformation of the test sample specimen. Cantilevered strain gauges 850, 851 are secured to arms 852, 853 which in turn are secured to the radial strain gauge ring 838. Wiring 846 is interconnected with and extends from the gauges 850, 851 (and others not shown) to the monitor/control computer. Pressure change is provided by a microaccumulator 884 which is in communication with the pore pressure port via a line 886. Wiring 892 extends from the microaccumulator 884 for interface with a monitoring system e.g. a computer which may also control the microaccumulator and record the details of its operation.

The apparatus 800 can be enclosed within a housing, now shown (such as the housing 615, FIG. 8) and used with a piston, not shown (such as the piston 613, FIG. 8) and a pumping system, not shown (such as the system 617, FIG. 8).

Figure 12:
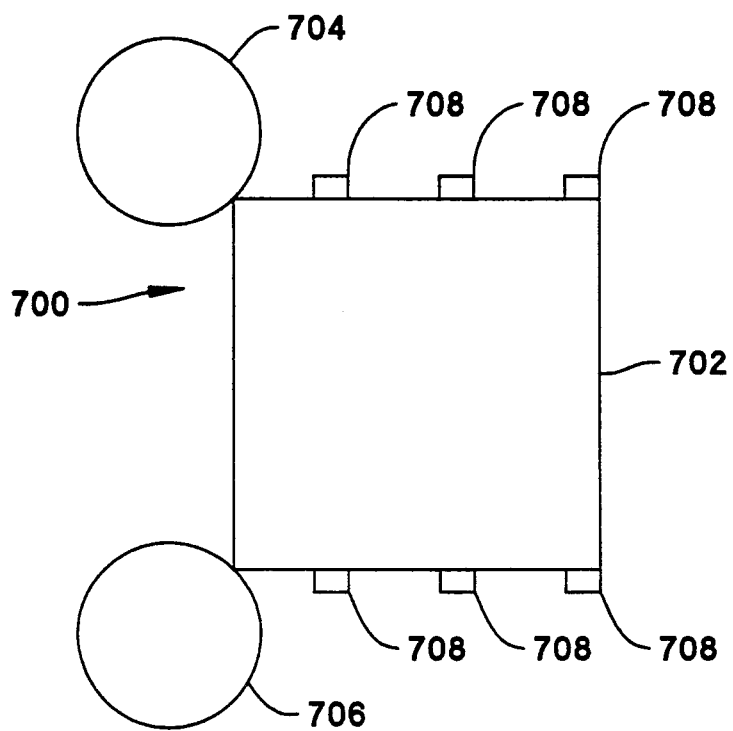
FIG. 12, 13 and 14 show schematically screen members.

To promote fluid movement to the pore pressure channel, a screen or screens partially or totally enclose the sample and are applied before applying the flexible jacket(s). As shown in FIG. 12, a screen member 700 according to the present invention for enclosing a sample to facilitate the flow of sample fluid therefrom has a main square portion 702 for encircling the side wall of a cylindrical sample and a cylindrical sample and two circular portions 704, 706 connected thereto for folding over the circular ends of a sample. Tabs 708 fold over the circular portions to provide further flow areas.

Figure 13:
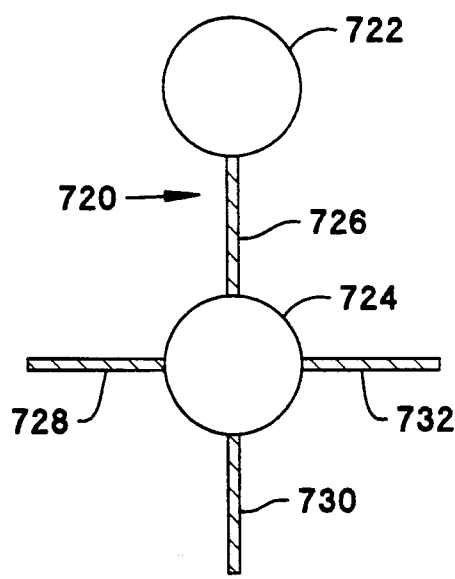

As shown in FIG. 13, the entire square portion 707 of the device in FIG. 12 is not needed to facilitate flow. A screen member 720 has two circular screen portions 722 and 724 interconnected by a thick piece of screen 726. Pieces of screen 728 and 730, and 732 extend from the circular portion 724 so that upon folding of the two circular portions onto the ends of a cylindrical sample the pieces 728, 730 and 732 are folded to contact the circular portion 722. Tabs may be used at the ends of the pieces 728, 730, and 732.

Figure 14:
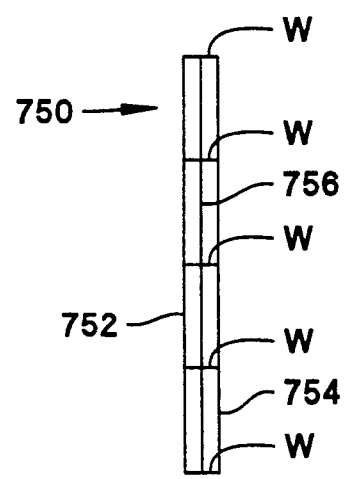

Any of the screens or pieces of screens in devices such as the screen members previously described can be formed from multi-component screens. For example, as shown in FIG. 14, a screen 750 has three screen components 752, 754, and 756 spot welded together at points W. The screens may be of different mesh. In the particular embodiment of FIG. 14, the screen 752 is 300 mesh and the screen 754 is 300 mesh. These relatively fine screens prevent the sample or the flexible jacket from entering the screen 756 which is of a coarser mesh, e.g. 100 mesh, thereby insuring that the screen 756 is not blocked and serves as a good flow path.

In conclusion, therefore, it is seen that the present invention and the embodiments disclosed herein are well adapted to carry out the objectives and obtain the ends set forth at the outset. Certain changes can be made in the method and apparatus without departing from the spirit and the scope of this invention. It is realized that changes are possible and it is further intended that each element or step recited in any of the following claims is to be understood as referring to all equivalent elements or steps for accomplishing substantially the same results in substantially the same or equivalent manner. It is intended to cover the invention broadly in whatever form its principles may be utilized. The present invention is, therefore, well adapted to carry out the objects and obtain the ends and advantages mentioned, as well as others inherent therein.

What is claimed is:

1. Triaxial test apparatus for testing material samples in a test cell with a housing fillable with confining fluid for providing confining pressure on a sample to be tested, the sample having a top and a bottom, the housing having a channel for introduction therein and removal therefrom of the confining fluid, the housing having an opening therethrough through which a portion of a load piston sealingly extends for providing a load on the sample, the triaxial test apparatus comprising
sample mounting means for mounting the sample within the housing, the sample mounting means including a top end cap for mounting at the top of the sample and a bottom end cap for disposition at the bottom of the sample,
the bottom end cap having a body and a pore pressure channel in the body in fluid communication with the bottom of the sample and into which flows sample fluid expelled from the sample during testing, the sample fluid contacting an inert fluid in the pore pressure channel,
a pore pressure chamber in the body in fluid communication with the pore pressure channel, the pore pressure chamber for containing an amount of the inert fluid,
a pore pressure transducer disposed in the pore pressure chamber for reacting to and sensing changes in the amount of sample fluid expelled from the sample during testing,
first wiring connected to the pore pressure transducer and extending therefrom and out of the body, the first wiring connectible to a system for monitoring and recording changes sensed by the pore pressure transducer,
the pore pressure channel and the pore pressure chamber filled with the inert fluid, the inert fluid immiscible with the sample fluid, at least one flexible impermeable jacket for enclosing the surface of the sample other than its ends and preventing the confining fluid from directly contacting the sample and preventing sample fluid from being expelled from the portion of the sample covered by the jacket, a first load cell mounted within the housing on top of the top end cap to indicate load on the sample, the bottom end cap suitable for mounting on a second load cell mounted within the housing, ultrasonic transducer means in each end cap mounted in a transducer recess in each end cap, each ultrasonic transducer means having transducer wiring extending therefrom and connectible to a system for monitoring and recording signals from the ultrasonic transducer means, and each ultrasonic transducer means mounted with an exposed portion at a face of the end cap adjacent the sample.

2. The triaxial test apparatus of claim 1 wherein the load cell comprises a load cell body with a ball recess therein, strain gauge means disposed in the load cell body beneath the ball recess, a ball removably disposed in the ball recess above the strain gauge means, and a portion of the ball extending above the load cell body for contact by a load inducing member.

3. A test method for triaxialy testing a low permeability rock sample, the sample prepared and mounted by mounting a pore pressure transducer in a pore pressure chamber in a bottom end cap of a triaxial test apparatus, the pore pressure chamber in fluid communication with a pore pressure channel extending to a surface of the end cap for disposition contactingly adjacent the rock sample to be tested, the pore pressure channel for receiving sample fluid expelled from the sample during testing, evacuating substantially all the air from the pore pressure channel and from the pore pressure chamber and then filling them with an inert fluid immiscible with the sample fluid, and in a sealed chamber, applying a screen member around the sample to facilitate the flow of sample fluid into the pore pressure channel, applying a flexible impermeable jacket to the sample, other than to its ends, and applying the bottom end cap to the bottom end of the sample and a top end cap to the top end of the sample, each end cap having an ultrasonic transducer mounted therein, and each ultrasonic transducer having transducer wiring leading therefrom connected to an exterior system for monitoring and recording signals from the sample, the sample having a pore pressure, the test method comprising placing the sample in a confinement vessel of a triaxial test apparatus and sealing the vessel shut, each end cap with a portion of the transducer exposed and contacting the rock sample, isostatically loading the sample by introducing a confining fluid under pressure into the confinement vessel to provide a constant confining pressure on the sample, interconnecting the pore pressure transducer and the ultrasonic transducers with the exterior system, allowing the sample's pore pressure to equilibrate and reach a substantially constant level as the sample consolidates under the pressure of the confining fluid, applying a load piston to the top end cap to apply a known load on the sample, the known load determined by placing a load cell on top of the sample between the load piston and the top end cap, the piston sealingly extending through the confinement vessel to contact the load cell, measuring and recording pore pressure of the sample continuously during the test, and measuring and recording ultrasonic velocities of ultrasonic waves transmitted from one ultrasonic transducer to the other through the sample continuously 4. A method for triaxially testing low permeability rock sample, the sample having pore pressure, the method comprising applying a top end cap to a top of the sample and a bottom end cap to a bottom of the sample, mounting a load cell on the top end cap, placing the sample in a confinement vessel of a triaxial test apparatus and sealing the vessel shut, isostatically loading the sample by introducing a confining fluid under pressure into the confinement vessel to provide a constant confining pressure on the sample, interconnecting pore pressure transducer means adjacent the sample with an exterior monitoring system, allowing the sample's pore pressure to equilibrate and reach a substantially constant level as the sample consolidates under the pressure of the confining fluid, applying a load piston to the load cell to apply a known load on the sample, the piston sealingly extending through the confinement vessel to contact the load cell, and measuring and recording pore pressure of the sample continuously during the test.

5. The method of claim 4 comprising also after applying the top end cap and the bottom end cap to the sample and prior to mounting the load cell on the top end cap applying ultrasonic transducers in each end cap for disposition contactingly adjacent the sample, and measuring and recording ultrasonic velocity of ultrasonic waves transmitted from top to bottom through the sample continuously during the test.

* * * * *